Oct. 16, 1934. V. LENS Plant Pat. 108
ROSE
Filed Dec. 26, 1933
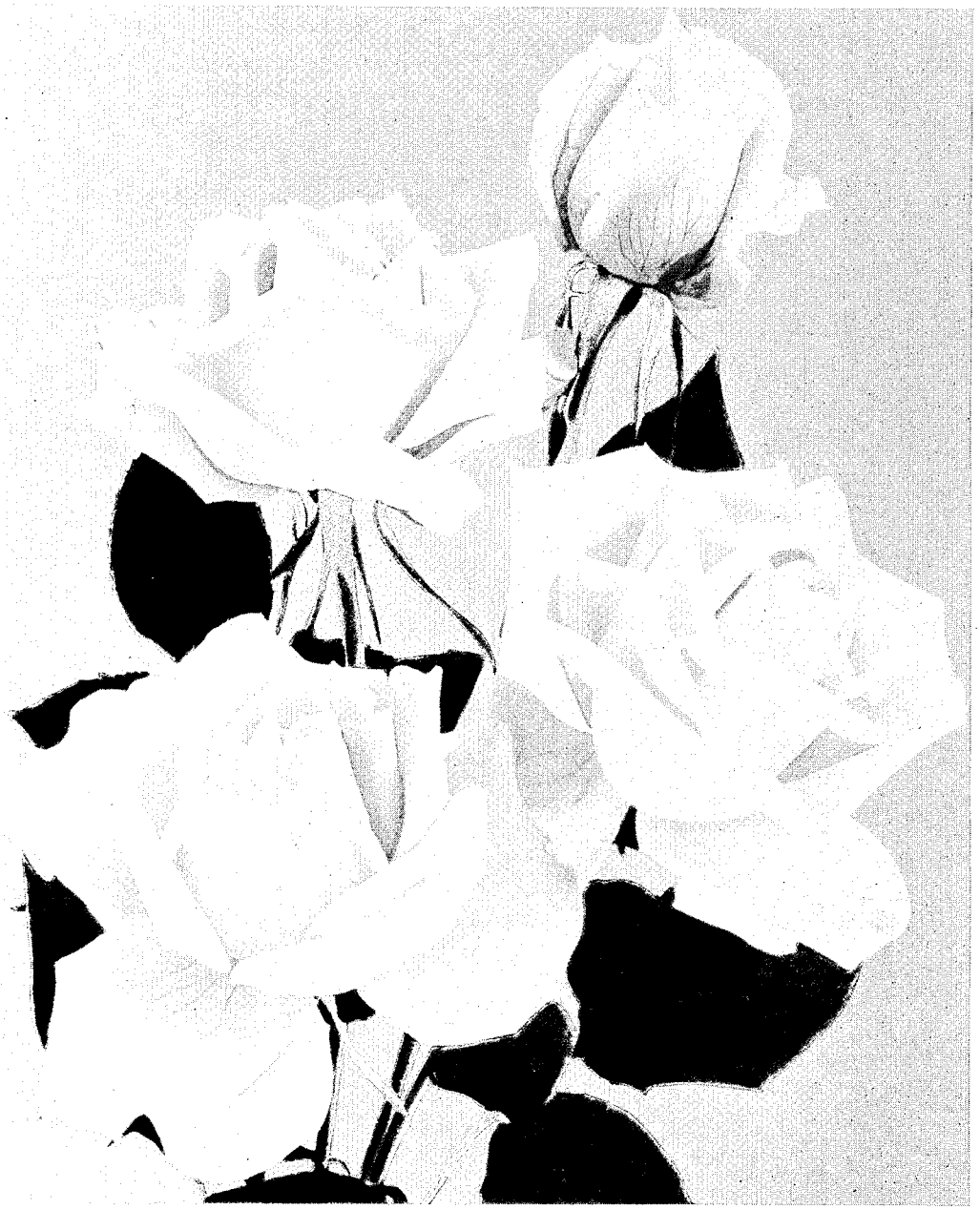
Inventor
Victor Lens
By Robb & Robb
Attorneys Patented Oct. 16, 1934

Plant Pat. 108

UNITED STATES PATENT OFFICE

108

ROSE

Victor Lens, Wavre Notre Dame, Belgium, assignor to Jackson & Perkins Company, Newark, N. Y.

Application December 26, 1933, Serial No. 703,988

1 Claim. (Cl. 47—61)

The present invention relates to an improvement in white roses, particularly adapted to greenhouse culture for cut flowers.

It is quite well known that the white rose has practically disappeared from greenhouses because none of the known varieties had the quality and steady production such as characterizes other roses of color and such as is necessary or desirable for greenhouse purposes.

The present rose has therefore been developed to fill the long desired demand, serving to bring back the white rose into favor as a cut flower. However, it is to be understood that this rose has also proved to be an improvement in and valuable addition to the line of garden roses.

The present rose, which has been asexually propagated and found to produce true to form, originated from a cross between unnamed seedlings issued from Briarcliff, Kaiserin Auguste Viktoria and Mrs. Herbert Stevens. The last named rose being a pure Tea rose, reinforces the Hybrid Tea strain and accounts for the unprecedented continuity and quantity of production which characterize this improvement rose.

Broadly speaking, the rose forming the subject matter of this application is considered novel in every particular, as to size, fragrance, form and length of stem required by the cut flower market.

Insofar as the bud is concerned, this is long pointed, the outer petals slowly recurve and the center of the bud remains tight for a very long period. The open bloom retains its form for days, thus enhancing its value as a cut flower. The production of commercial flowers is very heavy and steady. It is believed to be the finest white rose ever produced for forcing or garden use.

The above mentioned and other important characteristics are here listed for detail information:

Parentage—
- Seedling.
- *Seed parent.*—Unnamed seeding of Briarcliff and Kaiserin A. Viktoria.
- *Pollen parent.*—Unnamed seedling of Briarcliff and Mrs. Herbert Stevens.

Classification—
- Hybrid Tea.

*Flower*

Blooming habit—
- Continuously recurrent.

Bud—
- *Size.*—Very large.
- *Form.*—Long, ovoid; unaffected by wet or hot weather.
- *Color.*—White with greenish tint when sepals first divide. When half blown, inside of petals pure white with light yellow in depth; reverse of petals pure white.
- *Sepals.*—Serrated, curling back when bud half open.
- *Calyx.*—Funnel shape; broad; smooth and without odor when rubbed.
- *Peduncle.*—Length — very long. Aspect — smooth. Color — light green. Strength — erect; heavy.
- *Opening.*—Opens very well.

Bloom—
- *Size.*—Very large; average size when fully expanded four inches.
- *Borne.*—Singly.
- *Stems.*—Long; strong.
- *Form.*—When first open it is cupped; retains its form to the end; outer petals curl back.
- *Petalage.*—Double, the number of petals under normal conditions being about forty.
- *Color.*—Center of flower pure white. Outer petals pure white. Base of petals—white with extreme ends light yellow. Inside and reverse of petals pure white.

Petals—
- *Texture.*—Thick, unaffected by wet or hot weather.
- *Appearance.*—Inside shiny, satiny; outside, satiny.
- *Form.*—Round.
- *Arrangement.*—Imbricated; few petaloids in center.
- *Persistence.*—Drop off cleanly.
- *Fragrance.*—Moderate tea.
- *Lasting quality.*—On the plant and as a cut flower, very long.

Genital organs—
- *Stamens, anthers.*—Medium many, yellow color; arranged in regular around styles.
- *Stamens, filaments.*—Medium; white color.
- *Pollen.*—Lemon yellow.
- *Styles.*—Loosely separated; heavy.
- *Stigmas.*—White color.
- *Ovaries.*—All enclosed in calyx.

Fruit—
- Fertile.
- *Form.*—Ovoid, round headed.
- *Aspect.*—Smooth.
- *Color at maturity.*—Orange.
- *Sepals.*—Caducous.

*Plant*

Form—
- Bush.

Growth—
- Vigorous.

Foliage—
- Five, at times seven leaflets; large.
- *Quantity.*—Abundant.
- *Color.*—New foliage—upper side, dark green; under side, light green. Old foliage—upper side, normal green; under side, light green.
- *Shape.*—Oval pointed.

*Texture.*—Upper side, leathery; under side, rough.
*Edge.*—Serrated.
*Serration.*—Single, small.
*Leaf stem.*—Color, green; under side, smooth.
*Stipules.*—Medium; smooth.
*Disease resistance.*—Resistant, immune.

Wood—
*New wood.*—Color, light green; bark, smooth.
*Old wood.*—Color, green; bark, smooth.

Thorns—
*Thorns.*—Quantity—on main stalks from base, ordinary; on laterals, few. Form—broad base, medium, short, straight. Color when young, green and red. Position—irregular.
*Prickles.*—Quantity on main stalks, none; on laterals, none. Color, green, brown.
*Short needles.*—Quantity on main stalks, none and none on laterals.

I claim:—

The new and distinct variety of rose plant characterized by its particular adaptation to greenhouse culture for cut flowers where it produces evenly and continuously a quantity of blooms of high quality, thereby being of great value to the cut flower florists; by its large size, the fragrance of its bloom, its form, and length of stem, all as described, and the white color of its flower, as shown.

VICTOR LENS.